United States Patent [19]
Vanderbeeken

[11] Patent Number: 5,132,209
[45] Date of Patent: Jul. 21, 1992

[54] PROCESS FOR TESTING FOR MATERNAL-FETAL IMMUNOINCOMPATIBILITY IN PREGNANT WOMEN

[76] Inventor: Yves-E Vanderbeeken, 3475 Redpath Avenue, Montreal, Quebec, Canada, H3J 2J7

[21] Appl. No.: 95,678

[22] Filed: Sep. 14, 1987

[51] Int. Cl.$^5$ .......................................... G01N 33/567
[52] U.S. Cl. .................... 435/7.21; 435/7.23; 435/7.24; 435/810; 435/820; 435/948; 435/975; 436/503; 436/510; 436/811
[58] Field of Search ............... 436/501, 503, 504, 508, 436/528, 548, 811, 510; 435/7, 810, 948, 7.21, 7.23, 7.24, 820, 976

[56] References Cited

U.S. PATENT DOCUMENTS

| | | | |
|---|---|---|---|
| 3,720,760 | 3/1973 | Bennich et al. | 436/573 |
| 4,134,792 | 1/1979 | Boguslaski et al. | 436/537 |

OTHER PUBLICATIONS

Dausset, *Science*, 213, 1469–1474, 1981.
Lampson et al., *Journ. Immunol.*, 125, 293–299, 1980.
Nicholas et al., "Human Retroplacenal Sera Inhibit the Expression of Class II Major Histocompatibility Antigens", Journal of Reproductive Immunology, 9 (1986) 95–102.
Alberts et al., "Moledular Biology of the Cell", Garland Publishing, Inc.
Kajino et al., "Blocking Effects of Maternal Serum-IgG . . . Their Individual Specificity", American Journal of Reproductive Immunology, 4:27–32 (1983).
An Introduction to Radioimmunoassay and Related Techniques, T. Chard, vol. 6, part 2, 3rd revised edition, 1987.
Barrett, *Textbook of Immunology*, Third Edition, The C. V. Mosby Company, Saint Louis, 1978, pp. 394–395.
MacIntyre et al., Am. Jour. Reprod. Immunol. 10, 121–126, 1986.
Hamilton et al., Abstract from the 6th Annual Meeting, American Society for the Immunology of Reproduction, 1985, p. 129.
Takakuwa et al. Am Jour. Reprod. Immunol. 10 1–9, 1986.
Takeuchi et al., *IBID* p. 132.
1986 Becton Dickinson Monoclonal Catalogue, p. 9.
1985 Sigma Chemical Company Catalogue, p. 1110.
Scott et al. (Eds.) *Immunology in Obstetrics and Gynecology*, Appleton-Crofts-Century, p. 38.

*Primary Examiner*—David A. Saunders
*Attorney, Agent, or Firm*—Bacon & Thomas

[57] ABSTRACT

A kit for testing materno-fetal immunoincompatibility in women, particularly in women whose fetuses are in danger, comprises two containers containing an identical amoung of HLA-D antigen-containing material and one container containing male serum as control. In the test, maternal serum of the patient is added to one container of antigen while the control serum is mixed with the other container of antigen. The amount of expressed HLA-D antigen remaining in each case is established by conventional HLA-D directed monoclonal antibody immunoassay techniques such as conventional radioimmunoassay. The maternal serum assay divided by the control serum assay gives an immunoincompatibility quotient (IQ). The IQ is from 40 to 50% in healthy pregnant women and is about 70% in pathological cases. The test provides reliable results since the antigenic portion is non-living and therefore does not offer the inconstances of living test reagents.

3 Claims, 1 Drawing Sheet

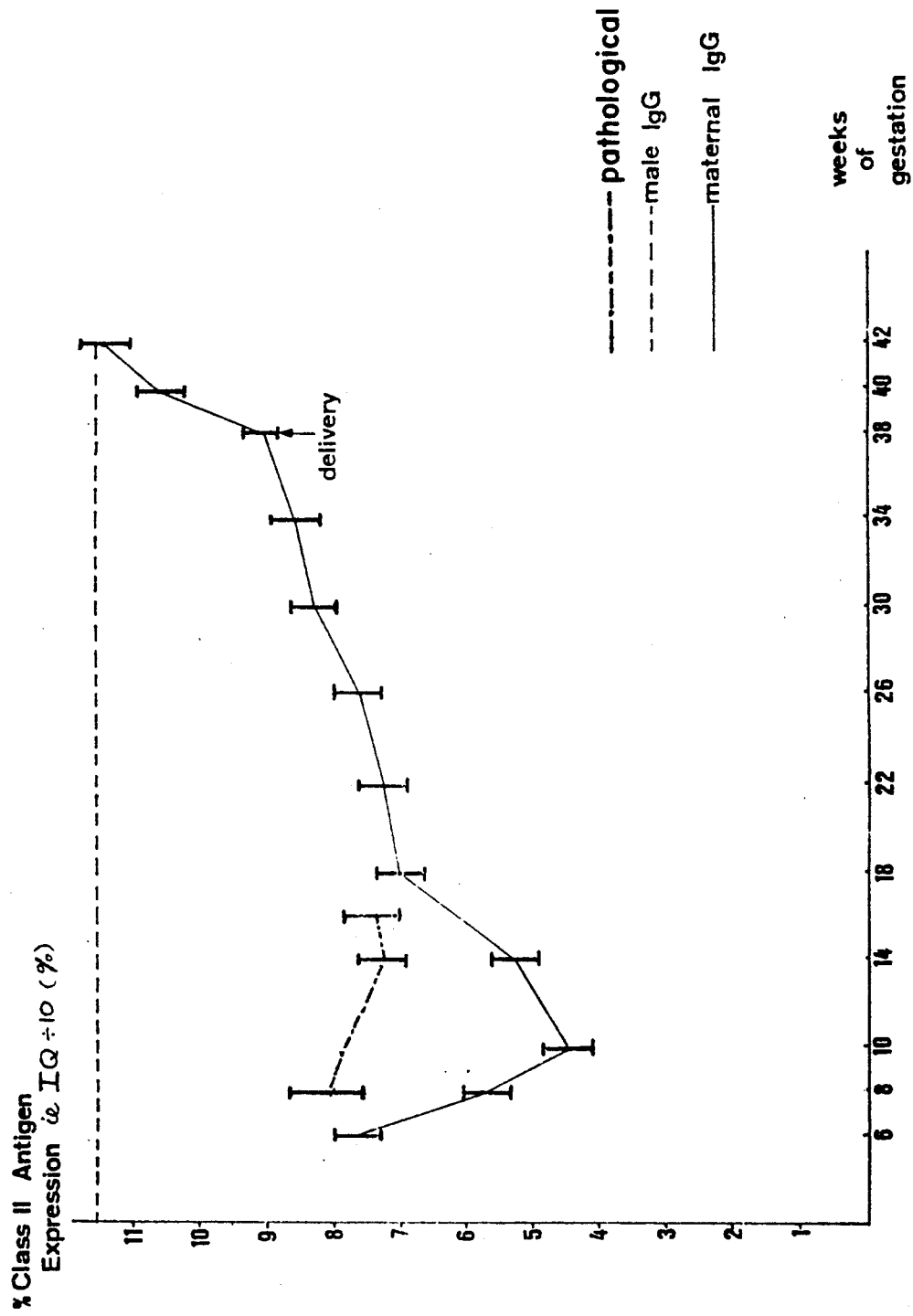

PROCESS FOR TESTING FOR MATERNAL-FETAL IMMUNOINCOMPATIBILITY IN PREGNANT WOMEN

BACKGROUND OF THE INVENTION (i) Field of the invention

This invention relates to a diagnostic kit useful in establishing the existence or potential existence of materno-fetal immunoincompatibility in women. The invention also relates to a method of preparing the kit, its constituents and to a method of using the kit.

(ii) Description of the Prior Art

In normal pregnancy, a fetus, despite being an immunologically separate entity from its mother, is not attacked by its mother's immune system. Thus a "host versus graft reaction" (HVGR) as in rejection of transplanted organs, does not occur.

In other words, the antigenic determinants of the fetus are not recognized by the mother's immune system. This is because the (blood) serum of the mother normally contains blocking substances which partially block the fetus' minor histocompatibility antigenic determinants rendering them "invisible" to the mother's immune system.

The maternal serum has this effect on several fetal antigens some of which are the class II histocompatibility antigens (otherwise known as HLA-Ds).

In normal pregnancy, fetal cells show diminished expression of these antigens because they are wholly or partially blocked by said blocking agents.

It has been observed that spontaneous miscarriages and certain kinds of infertility in women as well as the risk of preterm delivery result from the patients' inability to produce such blocking substances, i.e. the absence or reduction in amount of these substances in certain pathological cases causes the said miscarriages, infertility, or preterm delivery.

Patients suffering from past miscarriages or infertility and wishing to become pregnant or patients whose fetus is at risk, are presently treated by injection of mononuclear blood cells taken from their respective mates or from other healthy (male) donors.

Patients showing signs of impending preterm delivery (e.g. contractions) presently undergo intensive conservative treatment (e.g. bedrest and perfusion with beta-mimetic drugs) to avoid premature termination of their pregnancies.

The antigenic incompatibility of the type under discussion is mainly found in couples partly sharing HLA class I or HLA class II antigens.

Clearly, not all infertilities, miscarriages and preterm deliveries are caused by the above-described immunological problem and therefore not all patients can be successfully treated by the above-described injection of blood cells (in the first two cases) or by intensive conservative treatment (in the third case).

It is therefore desirable to have a means of selecting which patients may be susceptible to such treatments.

Such selection is presently done on a clinical basis (i.e. by exclusion) and also after a HLA class I and class II study. In other words, where no obvious organic, homonal or infectious etiology is demonstrated, it is assumed that an immunological insufficiency could be a possible etiology. Thus no positive diagnosis of immunological insufficiency is made, instead only indirect evidence is provided to support such a diagnosis.

Recently Alan BEER at the INSERM/CNRS Materno-Fetal Relationship Colloque held at the Clinique Universitaire Baudelocque on Oct. 18, 1986, in Paris, France, has proposed the use of a mixed lymphocyte reaction (MLR) - see page 38 of IMMUNOLOGY IN OBSTETRICS AND GYNECOLOGY by James R. SCOTT et al, pub. Appleton-Century-Crofts-as a diagnostic tool.

In this test, maternal lymphocytes are mixed with paternal lymphocytes. The HLA-D (class II) antigens on the paternal lymphocytes stimulate proliferation of the maternal lymphocytes. This proliferation is measured by the amount of DNA synthesis occuring in the maternal lymphocyte. In pathological cases DNA synthesis is increased over healthy cases since normally the paternal antigens are blocked by the blocking agent. Thus the test interprets increased DNA synthesis to mean lack, or reduced presence, of the blocking agent i.e. a pathological condition. However, BEER's test proved unreliable as it gave unreproducible results.

Another team, headed by J. F. Mowbray, has proposed a haemoagglutination test. This was described at the 3rd International Congress of Reproductive Immunology in Toronto, Canada, from July 1-5, 1986. However, this test does not measure the inhibitory effect of maternal serum.

In any event, the prior art test procedures all involve living cells in the test materials. This brings many problems such as possible infection of the materials, genetic mutation, inconstant phenotypic characteristics aswell as the concomitant problems of storage and short shelf-life. The above problems often result in unreliable and inconstant results.

OBJECTS OF THE INVENTION

It is an object of the present invention to provide a simple test for the diagnosis of materno-fetal immunoincompatibility in pregnant women.

It is also an object of this invention to provide a test for diagnosing impending preterm delivery in immunodeficient women.

It is another object of this invention to provide a diagnostic test to establish whether a patient has suffered a miscarriage when a delay in the menses is experienced.

It is a further object of the invention to provide a kit for carrying out the above tests.

Another object is to provide a process for producing the kit, and for using it in conducting the above-described tests.

A final object is the provision of a standard test material containing non-living matter and therefore not subject to concomitant inconstancy of characteristics.

SUMMARY OF THE INVENTION

In meeting these and other objects, the invention provides a diagnostic kit comprising:

two first containers each containing an identical amount of a material comprising class II histocompatibility antigens;

a second container containing a material comprising a control serum.

The invention also provides a process for measuring a materno-fetal immunoincompatibility quotient in women comprising:

A) mixing a sample, containing a first amount of maternal serum from a patient to be tested with a second amount of a material comprising class II histocompatibility antigens;

B) performing a first radioimmunoassy of expressed class II histocompatibility antigens in said mixture using anti-class II histocompatibility antigen directed monoclonal antibodies;

C) mixing a separate control sample containing said first amount of control serum with another of said second amounts of a material comprising class II histocompatibility antigens;

D) performing a second radioimmunoassay of expressed class II histocompatibility antigens in said control mixture using said monoclonal antibodies;

wherein said immunoincompatibility quotient (IQ) is given by the expression:

$$IQ = \frac{\text{assay of patient's serum}}{\text{assay of control serum}}.$$

The invention further provides a diagnostic test for the establishment of materno-fetal immunoincompatibility in women using the above-mentioned process.

One advantage of the present invention is that positive diagnosis of materno-fetal immunoincompatibility allows a more timely treatment of the afflicted person.

The present invention is based on the premise that in order to study the inhibitive function of maternal serum, one must avoid the use of living cells which as noted above give inconstant results. However a constant source of class II histocompatibility antigens is needed in order to give reproducible results. "Thus the present invention uses a constant (i.e. uniform or stable) source of Class II histocompatibility antigens in order to give reproeducible results."

This source of antigens may be in free form, in solution or suspension, attached to an organic or other substrate or otherwise supported. Supported antigens may further be suspended or in solution.

A preferred source of antigens are pieces of cellular membranes carrying the class II histocompatibility antigens, i.e. the antigens are supported.

With this in mind, a particularly preferred membrane source is a neoplastic B cell line. Such cell lines are useful because they have a high and constant cellular expression of class II histocompatibility antigens.

The membranes prepared according to this embodiment, may be stored in discrete vessels, each vessel containing enough reagent for a test according to the invention.

By this means, all the prior art problems presented by viable cells, like infections, poor culture, inconstant class II antigen presentation and time consuming laboratory work, have been avoided.

The invention also relies on the need for a control or reference test value in order to compare the inhibitive activity of the maternal serum with a standard. It is preferred that this standard be a pool of human male serum because, in the test, it gives constant low values of inhibitive activity. However, the serum of non-pregnant women not taking the contraceptive pill, may also be used. The serum of other animals may also be used, veal serum being preferred.

BRIEF DESCRIPTION OF THE DRAWING

FIG. 1 is a graphical representation of the inhibitive activity of healthy and pathological maternal serum during gestation.

In FIG. 1, the percentage of class II antigen expression (IQ) is plotted against the number of weeks of gestation. Three traces are shown. The male serum, as noted above, gives constant high values of antigen expression (i.e. low inhibitive properties) and is represented by the horizontal are also shown. Note that the values are actually for IgG which is found to be the active blocking agent in serum. The test according t.,o the invention, is designed in one aspect, to appraise immunoincompatibility in patients up to 26 weeks pregnant. After that time, the serum of pregnant mothers reaches a constant value (IQ≈70%) in its antigenic suppressive properties - see FIG. 1. As a result the difference in IQ between healthy and pathological mothers is less marked after 26 weeks although an IQ above 70% can still be considered a pathological diagnosis. However most miscarriages due to immunoincompatibility occur in the 4th to 14th weeks of pregnancy, when, therefore, diagnosis is most desirable. In this 4 to 14 week period the IQ for healthy women is as low as 40% to 50%, therefore IQ figures above these values may indicate a pathological condition.

However for the suspected preterm delivery patients, diagnosis is useful after the 26th week. In this case if the patients' IQ is above 70% then it amounts to a positive diagnosis and an indication that immediate conservative treatment should commence.

The test may also be used to establish whether or not a miscarriage has occurred, when the patient experiences a delay in the menses. For Rh negative patients, a positive diagnosis under such circumstances would signal the need for immediate RhD antibody treatment and thereby allow such patients to conceive again before the mother becomes alloimmune.

DETAILED DESCRIPTION OF THE INVENTION

A preferred way of preparing the kit according to the invention is to isolate neoplastic B cells (eg the RAJI, DAUDI and JURKAT cell lines) which are then crushed to obtain pieces of cellular membranes. The mixture is then subjected to centrifugation whereafter the cellular particles are collected and lyophilised. Ultracentrifugation is preferred.

A portion of the resulting solution is encapsulated in a vial at an effective concentration in a physiologically acceptable medium ranging from $10^5$ to $10^7$ cell/ml, and then stored at low temperature. This is vial n° 1. Next a 0.5 to 50% dilution of control serum, in a physiologically acceptable medium is placed in a second vial which is then stored in a frozen state. This is vial n° 2. The control serum may be from non-pregnant, non-contraceptive pill-taking women or may simply be human male serum. In this last case, the male serum can be a sample from a seric pool provided by at least 10 healthy males. However the control serum need not be human serum but could be for instance bovine serum. Specific examples of suitable sera are found in the Feb. 1985 catalogue of the SIGMA ® Chemical Company under numbers P7656 and 540-10 on page 1110.

The first half of the test, according to the invention, is carried out by mixing a sample of maternal serum to be tested, with the contents of vial n° 1 (antigens). The mixture is then incubated.

Some of the antigens will be blocked by the blocking factor in the maternal serum. To establish the extent of blocking (and thereby whether the patient is healthy) a classical radioimmunoassay is carried out as described, for instance, on page 4 et seq of "Laboratory Techniques in Biochemistry and Molecular Biology" 3rd edition, (1987) by T. Chard, pub. Elsevier. The assay measures the quantity of antigens being expressed.

For this assay anti-class II histocompatibility antigen directed monoclonal antibodies are used eg anti IA, anti-DP, anti-DR or anti-DQ. Suitable examples are given on page 9 of BECTON DICKINSON's 1986 "Monoclocal Catalog".

The second half of the test (to establish the control value) is carried out by performing the same procedures as for the first half of the test, but with a vial of control serum (vial no° 2) and the second vial no° 1 (antigen).

The amount of maternal serum taken in the first half of the test is the same as the amount of control serum contained in vial no° 2.

Example

Vials containing membranes carrying class II histocompatibility antigens were prepared in the following stages:

1. Homogenise RAJI cells (1 g/10 ml) in 0.25 M sucrose in a buffer which contains 3 mM $CaCl_2$, 3 mM tris-HCl (pH 8.0), 50 mM $NaHSO_3$, 1 mM PMSF. Homogenise the cell suspensions in a motor-driven Teflon®-glass Potter-Elvejhem homogeniser (clearance 0.15–0.23 mm) at 1200 rev/min using one stroke.

2. Filter the homogenate through a Nitex filter with 100 μm pores and centrifuge the remaining solid portion at 1000xg for 10 min at 5° C.

3. Dilute the resulting material to an effective membrane concentration of $10^6$ cell/ml and store in airfree vials at 0° C. (vial no° 1).

Testing 0.5 $cm^3$ of a 10% solution of a maternal serum to be tested, is mixed with the contents of a first vial no° 1. The mixture was incubated at 37° C. for three days.

The remaining (unblocked) expression of class II antigen is then examined using HLA-DR directed monoclonal antibodies in a radioimmunoassay as noted above.

The control value is established by performing the same test but with a vial containing 0.5 $cm^3$ of 10% solution of control serum (vial no° 2) and a second, identical antigen-containing vial (no° 1).

The above test was done for a number of healthy pregnant women. In each case the value of the assay for the tested maternal serum, divided by the value of the assay for the control serum was established, and gave a mean value ranging from 40 to 50% with an SD of ±18 (p<0.01). This value is termed the immunoincompatibility quotient (IQ). The tests were made on women 4 to 14 weeks pregnant. The IQ of healthy pregnant women after the 14th week of pregnancy, is from 30 to 40% (SD±10%, P—0.01).

In an identical test done on women showing pathological symptoms (miscarriage and infertility) the IQ was over 70%. The results of four such women are given in table 1.

IQ (%) in Pathological cases.

TABLE 1

| Patient No. | Gestation (weeks) | | | | | |
| --- | --- | --- | --- | --- | --- | --- |
| | 6 | 7 | 8 | 10 | 14 | 16 |
| 1 | — | 78 | — | 69 | 71 | — |
| 2 | — | — | 61 | — | 87 | 83 |
| 3 | — | — | 57 | — | 89 | 59 |
| 4 | 74 | — | — | — | 69 | 78 |

Although the present invention has been described hereinabove by means of preferred embodiments thereof, it should be pointed out that any modification to these preferred embodiments, within the scope of the appended claims, is not deemed to change or alter the nature of the invention.

What is claimed is:

1. A diagnostic kit for assaying th blocking effect of maternal serum on human class II histocompatibility antigens, said kit comprising:
   a supply of class II histocompatibility antigens other than class II histocompatibility antigens on while viable cells;
   a supply of a material comprising a non-maternal control serum which is ale to block said antigens to give a constant low value of said blocking effect, lower than for said maternal serum wherein said control serum is human male serum or human serum from at least one non-pregnant, no-contraceptive pill-taking woman.

2. A kit according to claim 1 wherein said material comprising class II histocompatibility antigens comprises membranes which originate from at least one neoplastic B cell line.

3. A kit according to claim 2, wherein the cell line is selected from the group consisting of RAJI, DAUDI and JURKAT cell lines.

* * * * *